(12) United States Patent
Kahn

(10) Patent No.: US 6,586,605 B1
(45) Date of Patent: Jul. 1, 2003

(54) PURIFICATION OF ALKYLENE CARBONATE

(75) Inventor: Andrew P. Kahn, Eagleville, PA (US)

(73) Assignee: Arco Chemical Technology, L.P., Greenville, DE (US)

(*) Notice: Subject to any disclaimer, the term of this patent is extended or adjusted under 35 U.S.C. 154(b) by 0 days.

(21) Appl. No.: 10/339,748

(22) Filed: Jan. 8, 2003

(51) Int. Cl.[7] ............................................. C07D 317/36
(52) U.S. Cl. ........................................ 549/230; 203/29
(58) Field of Search ............................ 549/230; 203/29

(56) References Cited

U.S. PATENT DOCUMENTS

| | | | |
|---|---|---|---|
| 2,773,070 A | 12/1956 | Lichtenwalter et al. | 260/340.2 |
| 2,773,282 A | 12/1956 | Backer | 18/8 |
| 4,786,741 A | 11/1988 | Sachs | 549/230 |
| 5,283,356 A | 2/1994 | Marquis et al. | 558/260 |
| 5,405,977 A | 4/1995 | Cuscurida et al. | 549/541 |
| 5,631,386 A | 5/1997 | Gupta | 549/228 |
| 5,962,699 A | 10/1999 | Marquis et al. | 549/230 |
| 6,384,240 B1 | 5/2002 | Machac, Jr. et al. | 549/230 |

*Primary Examiner*—Taofiq Solola
(74) *Attorney, Agent, or Firm*—Kevin M. Carroll

(57) ABSTRACT

The invention is a method to purify an alkylene carbonate such as propylene carbonate by contact with at least two solid adsorbents comprising carbon and an inorganic silicon or aluminum oxide. The purification method successfully improves color and color stability while also reducing the amount of catalyst impurity contained in the alkylene carbonate.

13 Claims, No Drawings

PURIFICATION OF ALKYLENE CARBONATE

FIELD OF THE INVENTION

This invention relates to the purification of an alkylene carbonate such as propylene carbonate by contact with at least two solid adsorbents comprising carbon and an inorganic silicon or aluminum oxide. Surprisingly, the combination of carbon with an inorganic silicon or aluminum oxide removes trace amounts of the catalyst used to make the alkylene carbonate while simultaneously improving color and color stability in the alkylene carbonate.

BACKGROUND OF THE INVENTION

It is well-known to form an alkylene carbonate by the reaction of an alkylene oxide with carbon dioxide. A wide variety of catalysts and reaction conditions are taught in the prior art. Particularly useful catalysts include halide containing catalysts such as organic quaternary ammonium halides, organic quaternary phosphonium halides, organic sulfonium halides, and organic antimony halides. See, for example, U.S. Pat. Nos. 2,773,070, 4,786,741 and the like.

A problem associated with prior practices is the color instability of the alkylene carbonate as well as contamination of the alkylene carbonate with various impurities. Alkylene carbonates prepared by the above known procedures typically contain small amounts of the catalyst used in the alkylene carbonate production process. In addition to the trace amounts of catalyst impurities, alkylene carbonates prepared by the above procedures also tend to develop discoloration. The exact cause of the color instability is not known with certainty, although it is believed that at least a factor contributing to the color instability is the presence of small amounts of nitrogen and/or halide compounds derived from the catalyst used in production of the alkylene carbonate.

The catalyst impurity and the color instability problems have an important and adverse effect on the sale and use of such products. Thus, efforts have focused on developing methods to reduce catalyst impurities and improve color and color stability.

For example, U.S. Pat. No. 5,962,699 describes a process for decolorizing alkylene carbonates by contacting with hydrogen peroxide. U.S. Pat. No. 5,405,977 discloses the use of hydrotalcites to remove organic halide impurities in alkylene carbonates. U.S. Pat. No. 6,384,240 describes a process to provide high purity alkylene carbonate through use of multiple distillations. It also discloses that the high purity alkylene carbonate may be further purified by use of high surface area carbon to improve the UV absorbance of the alkylene carbonate. However, unlike the process of this invention, the process of U.S. Pat. No. 6,384,240 is not effective for the simultaneous removal of catalyst residues.

In sum, new processes for the purification of alkylene carbonates are needed. Particularly useful processes will improve the color and color stability of the alkylene carbonate while also removing catalyst impurities in the alkylene carbonate. I have discovered an effective, convenient purification process that both improves color and removes catalyst impurities.

SUMMARY OF THE INVENTION

The invention is a method of purifying alkylene carbonate. The method comprises contacting the alkylene carbonate with at least two solid adsorbents comprising carbon and an inorganic silicon or aluminum oxide. The method surprisingly reduces the color in the alkylene carbonate while also removing the catalyst used to produce the alkylene carbonate.

DETAILED DESCRIPTION OF THE INVENTION

Alkylene carbonates treated by the invention are prepared using known reagents, catalysts and reaction conditions. See, for example, U.S. Pat. Nos. 2,773,282, 4,786,741 and the like, the disclosures of which are incorporated herein by reference.

Particularly, the invention is applicable to the treatment of alkylene carbonates prepared by the reaction of alkylene oxide with carbon dioxide in the presence of organic quaternary ammonium halides, organic quaternary phosphonium halides, organic sulfonium halides, and organic antimony halides catalysts. The invention is especially applicable to the treatment of propylene carbonate and ethylene carbonate prepared by the tetraethyl ammonium bromide catalyzed reaction of propylene oxide with carbon dioxide and ethylene oxide with carbon dioxide.

As described in U.S. Pat. No. 5,283,356, the disclosure of which is incorporated herein by reference, the reaction of an alkylene oxide and carbon dioxide to form alkylene carbonate may be carried out at a temperature of from about 100° to about 225° C. or higher, preferably from about 175° to about 215° C. The reaction may be carried out at atmospheric pressure or, advantageously, under a pressure of about 300 psig or greater. More preferably, the reaction is carried out under a pressure of about 300 to about 3000 psig. The reaction may be conducted either batch-wise or continuously.

In a continuous reaction, the alkylene oxide and carbon dioxide are introduced to a continuous reactor containing the catalyst, from which a portion of the reaction mixture may be continuously recirculated through the reactor. Another portion of this reaction mixture is continuously withdrawn and treated to remove unreacted alkylene oxide from product alkylene carbonate. Alternatively, the continuous reaction can be carried out on a once through basis with suitable heat removal.

Alternatively, batches of the alkylene oxide and catalyst may be introduced into an autoclave or kettle type reactor. The desired pressure may be built up by introducing carbon dioxide. Typically, the reaction mixture is heated to reaction temperature, agitated, and held under a super atmospheric pressure of carbon dioxide. After the bulk of the alkylene oxide has reacted, the reaction mixture can be treated to remove unreacted alkylene oxide.

The alkylene oxide and carbon dioxide should be mixed in proportion to provide an excess of carbon dioxide over and above the stoichiometric amount required for reaction. This excess may be on the order of from about 1.1 moles of carbon dioxide per mole of alkylene oxide to about 10 moles of carbon dioxide per mole of alkylene oxide. An excess of alkylene oxide should be avoided, because it results in undesired by-products, chiefly alkylene oxide polymer, and because explosive conditions may result.

After completion of the desired reaction between the alkylene oxide and carbon dioxide to form alkylene carbonate, the reaction mixture is treated to remove residual unreacted alkylene oxide. Advantageously, the system pressure is reduced and carbon dioxide and alkylene oxide are vented from the system. Even after such venting the reaction mixture contains unacceptable levels of alkylene oxide, usually from 0.1% to 1% or more as against acceptable levels of 0.06% or less. Simple flashing and removal of flashed alkylene oxide and carbon dioxide is generally ineffective in producing acceptable product. The stripping procedure of U.S. Patent No. 5,631,386 can advantageously be used.

Alkylene carbonates prepared by the above known procedures typically contain small amounts of the catalyst used in the reaction to produce alkylene carbonate. In addition to the trace amounts of catalyst impurities, alkylene carbonates prepared by the above procedures also tend to develop discoloration and this has an important and adverse effect on the sale and use of such products. The exact cause of the color instability is not known with certainty, although it is believed that at least a factor contributing to the color instability is the presence in the alkylene carbonate of small amounts of nitrogen and/or halide compounds derived from the catalyst used in production of the alkylene carbonate. As a measure of the color of a transparent compound, it is usual to report the APHA color number. A higher APHA color indicates higher color content.

In order to reduce the level of catalyst impurities and to improve the color and color stability of an alkylene carbonate, the alkylene carbonate is contacted in the liquid phase with at least two solid adsorbents. The adsorbents useful in the invention are carbon and at least one inorganic silicon oxide or aluminum oxide.

The carbon adsorbent used in the practice of the invention includes elemental carbon in various forms. Elemental carbon is known to exist in a variety of forms, including amorphous forms such as soot, carbon black, charcoals, and lampblack. Preferred carbons include activated carbon, charcoal, or attapulgite. Exceptionally useful activated carbons or charcoals include those obtained from lignite, gas black, coconut, bagasse, wood, sawdust, peat, pulp-mill waste, blood, bone, etc.

Specific activated carbons include Calgon Corporation granular carbons such as Calgon CAL, APC and F 400, NORIT granular activated carbons such as NORIT C, Cenco activated carbons, products of Central Scientific Company, Nuchar activated carbons, products of West Virginia Pulp and Paper Company, and products of Darco Division, ICI AMERICAS, Inc. A preferred property of the suitable carbon is a high specific surface area in the range of 900–1400 $m^2/g$ as it permits the maximum adsorption of impurities from the feed solution.

In addition to the carbon adsorbent, alkylene carbonate is also contacted with an inorganic silicon oxide, an inorganic aluminum oxide, or mixtures thereof. The inorganic silicon oxide for purpose of this invention is a solid material that contains a major proportion of silica (silicon dioxide). Amorphous (i.e., non-crystalline) silicon oxides are particularly preferred for use. In general, suitable inorganic silicon oxides are further characterized by having a relatively large surface area in relation to their mass. The term used herein and one normally used in the art to express the relationship of surface area to mass is "specific surface area". The inorganic silicon oxides for purpose of this invention have a specific surface area of at least 1 $m^2/g$, and preferably the average specific surface area is from 25 $m^2/g$ to 1000 $m^2/g$, and most preferably from about 50 $m^2/g$ to 400 $m^2/g$. The inorganic silicon oxides are porous, in that they have numerous pores, voids, or interstices throughout their structures. The most preferred inorganic silicon oxide is silica.

The inorganic aluminum oxide for purpose of this invention is a solid material that contains a major proportion of alumina (aluminum oxide) and have a specific surface area of at least 0.5 $m^2/g$, and preferably from 1 $m^2/g$ to 1000 $m^2/g$, and most preferably from about 50 $m^2/g$ to 400 $m^2/g$. Preferred inorganic aluminum oxides include various forms of alumina including α-alumina, γ-alumina, activated aluminas, and basic aluminas. Activated aluminas are partially hydroxylated aluminum oxide whose chemical compositions can be represented by the formula $Al_2O_{(3-x)}(OH)_{2x}$, where x ranges from about 0 to 0.8. Basic alumina as used herein refers to alumina having a surface area of 50–400 $m^2/g$ which has been impregnated with a basic solution having a pH of at least 9 and dried. The basic solution may suitably be a solution of an alkali metal or ammonium compound such as one selected from hydroxides, carbonates, bicarbonates, phosphates, and organic acid salts. Suitable basic compounds that may be employed include sodium, potassium or ammonium carbonate, hydroxide, bicarbonate, nitrate, formate, acetate, benzoate or citrate.

The adsorptive contact is conveniently carried out at temperatures in the range of about 15° C. to 90° C., preferably 20° C. to 40° C. Flow rates of about 1 to 10 volumes of alkylene carbonate per volume of adsorbent per hour, preferably 2 to 5 are preferred.

The carbon and inorganic oxide adsorbent may be mixed together in a single adsorbent contact bed. Separate beds of carbon and the inorganic oxide may also be employed. It is generally preferred to employ more than one adsorbent contact beds so that a depleted bed can be regenerated while a fresh bed is used. Regeneration can be by washing with water followed by drying or by stripping with a heated inert gas such as steam, nitrogen or the like.

The use of a carbon and at least one inorganic oxide reduces the level of catalyst impurities and to improve the color and color stability of an alkylene carbonate. Preferably, the first bed volume of alkylene carbonate passed over the solid adsorbent results in the removal of greater than 90% APHA color and greater than 80% halide from the feed alkylene carbonate. For example, Example 1 shows that the first bed volume of propylene carbonate passed over a carbon and silica bed removes 94% APHA color and 90% Br. As used herein, bed volume means the volume equal to the volume of solid adsorbents contained in the processing vessel.

The following examples merely illustrate the invention. Those skilled in the art will recognize many variations that are within the spirit of the invention and scope of the claims.

EXAMPLES 1–5

Adsorption Runs

A 1 cm ID glass column is packed with adsorbent. A feed of propylene carbonate (For Example 1: APHA=475, 210 ppm N, 1000 ppm Br; for the Comparative Examples 2–5: APHA=430, 180 ppm N, 1020 ppm Br) is then passed through the bed at a LHSV of approximately 2.2 hr-1 and product is collected in 50 cc cuts. The product is analyzed for APHA color (ASTM D1209) and amounts of N and Br.

Example 1 uses a mixed bed containing $SiO_2$ (GRACE Davison, SA=310 $m^2/g$) and Calgon CAL 12×40 carbon (SA=1050–1200 $m^2/g$). Comparative Example 2 uses Engelhard Al13996R Alumina (SA=~200 $m^2/g$). Comparative Example 3 uses $SiO_2$ (GRACE Davison, SA=310 $m^2/g$). Comparative Example 4 uses Calgon CAL 12×40 carbon. Comparative Example 5 uses Calgon APC 12×40 carbon (SA=1300–1400 $m^2/g$).

Table 1 lists the amounts of adsorbent(s) used in the adsorption runs, the adsorbent volume and LHSV. Table 2 lists the APHA color and amounts of N and Br.

TABLE 1

Adsorption Run Data

| Run # | Adsorbent(s) | Adsorbent Amount (g) | Adsorbent Volume (cc) | LHSV ($h^{-1}$) |
|---|---|---|---|---|
| 1 | $SiO_2$ | 8.5 | 23 | 2.2 |
|   | C | 9.4 | 23 |   |
|   |   |   | Total = 46 |   |
| 2* | $Al_2O_3$ | 23.4 | 46 | 2.1 |
| 3* | $SiO_2$ | 16.3 | 44 | 2.1 |
| 4* | C | 17 | 41 | 2.2 |
| 5* | C | 14.1 | 41 | 2.3 |

* Comparative Example

TABLE 2

Adsorption Results

| Run # | Cut # | APHA | APHA removed (%) | N (ppm) | N removed (%) | Br (ppm) | Br removed (%) |
|---|---|---|---|---|---|---|---|
| 1 | 1 | 28 | 94 | 8 | 96 | 100 | 90 |
|   | 2 | 80 | 83 | 58 | 72 | 400 | 60 |
|   | 3 | 121 | 74 | 110 | 47 | 500 | 50 |
|   | 4 | 157 | 67 | 140 | 33 | 700 | 70 |
| 2* | 1 | 127 | 70 | 8 | 95 | 90 | 91 |
|   | 2 | 219 | 49 | 33 | 82 | 300 | 70 |
|   | 3 | 265 | 38 | 79 | 56 | 600 | 41 |
|   | 4 | 296 | 31 | 110 | 39 | 800 | 22 |
| 3* | 1 | 99 | 77 | 3 | 98 | 100 | 90 |
|   | 2 | 154 | 64 | <2 | 99 | 200 | 80 |
|   | 3 | 231 | 46 | 15 | 92 | 200 | 80 |
|   | 4 | 308 | 28 | 150 | 17 | 300 | 70 |
| 4* | 1 | 43 | 90 | 110 | 39 | 700 | 31 |
|   | 2 | 71 | 83 | 130 | 28 | 900 | 12 |
|   | 3 | 104 | 76 | 140 | 22 | 900 | 12 |
|   | 4 | 119 | 72 | 150 | 17 | 900 | 12 |
| 5* | 1 | 53 | 88 | 110 | 39 | 700 | 31 |
|   | 2 | 82 | 91 | 130 | 28 | 900 | 12 |
|   | 3 | 114 | 73 | 150 | 17 | 900 | 12 |
|   | 4 | 126 | 71 | 140 | 22 | 900 | 12 |

*Comparative Example

The absorption results show that the use of an adsorbent bed that contains both silica and carbon reduces both APHA and the amount of N and Br remaining in the propylene carbonate. In contrast, a carbon, silica, or alumina bed by itself does not simultaneously lower both the APHA numbers and the amount of Br and N impurities. Since the first 50 cc cut is approximately one bed volume, the first bed volume of a carbon and silica bed removes 94% APHA color, 96% N, and 90% Br. In comparison, the first bed volume of carbon alone removes approximately 90% APHA color but only 39% N, and 31% Br. Alumina removes 95% N and 91% Br, but only 70% APHA color. Silica removes 98% N and 90% Br, but only 77% APHA color.

I claim:

1. A method of treating an alkylene carbonate which comprises contacting the alkylene carbonate in the liquid phase with carbon and an inorganic oxide selected from the group consisting of inorganic silicon oxide, inorganic aluminum oxide, and mixtures thereof at conditions effective to improve the color of the alkylene carbonate and to remove catalyst impurities therefrom.

2. The method of claim 1 wherein the alkylene carbonate is propylene carbonate.

3. The method of claim 1 wherein the alkylene carbonate is ethylene carbonate.

4. The method of claim 1 wherein the carbon has a surface area in the range of from about 900 to about 1400 $m^2/g$.

5. The method of claim 1 wherein the inorganic silicon oxide is amorphous silicon oxide.

6. The method of claim 5 wherein the inorganic silicon oxide has a surface area in the range of from about 50 to about 400 $m^2/g$.

7. The method of claim 1 wherein the inorganic aluminum oxide is selected from the group consisting of α-alumina, γ-alumina, activated alumina, and basic alumina.

8. The method of claim 7 wherein the inorganic aluminum oxide has a surface area in the range of from about 50 to about 400 $m^2/g$.

9. The method of claim 6 wherein the inorganic aluminum oxide is basic alumina.

10. A method of treating propylene carbonate which comprises contacting the propylene carbonate in the liquid phase with carbon and an inorganic oxide selected from the group consisting of amorphous silicon oxide, an inorganic aluminum oxide, and mixtures thereof at conditions effective to improve the color of the propylene carbonate and to remove catalyst impurities therefrom, wherein the carbon has a surface area in the range of from about 900 to about 1400 $m^2/g$ and the inorganic oxide has a surface area in the range of from about 50 to about 400 $m^2/g$.

11. The method of claim 10 wherein the amorphous silicon oxide is silica.

12. The method of claim 10 wherein the inorganic aluminum oxide is selected from the group consisting of α-alumina, γ-alumina, activated alumina, and basic alumina.

13. The method of claim 12 wherein the inorganic aluminum oxide is basic alumina.

* * * * *